(12) United States Patent
Richter et al.

(10) Patent No.: US 10,278,713 B2
(45) Date of Patent: May 7, 2019

(54) MEDICAL INSTRUMENTATION (71) Applicant: Aesculap AG, Tuttlingen (DE)

(72) Inventors: Berna Richter, Muehlheim (DE); Henning Windhagen, Hannover (DE)

(73) Assignee: Aesculap AG, Tuttlingen (DE)

( * ) Notice: Subject to any disclaimer, the term of this patent is extended or adjusted under 35 U.S.C. 154(b) by 453 days.

(21) Appl. No.: 15/149,268

(22) Filed: May 9, 2016

(65) Prior Publication Data

US 2016/0249939 A1 Sep. 1, 2016

Related U.S. Application Data

(63) Continuation of application No. PCT/EP2014/074253, filed on Nov. 11, 2014.

(30) Foreign Application Priority Data

Nov. 13, 2013 (DE) .................. 10 2013 112 497

(51) Int. Cl.
*A61B 17/17* (2006.01)
*A61B 17/16* (2006.01)
(Continued)

(52) U.S. Cl.
CPC ...... *A61B 17/1746* (2013.01); *A61B 17/1666* (2013.01); *A61B 17/56* (2013.01);
(Continued)

(58) Field of Classification Search
CPC ........ A61B 2034/108; A61B 2017/568; A61B 17/1746; A61B 17/1666
See application file for complete search history.

(56) References Cited

U.S. PATENT DOCUMENTS 5,919,195 A * 7/1999 Wilson ............... A61B 17/1666
606/80
6,305,885 B1 * 10/2001 Linthicum .......... B23B 51/0426
408/1 R
(Continued)

FOREIGN PATENT DOCUMENTS

CN 202078365 12/2011
DE 10335388 6/2006
(Continued)

OTHER PUBLICATIONS

Chen, et al., "Personalized image-based templates for precise acetabular prosthesis placement in total hip arthroplasty: a pilot study", Journal of Zhejiang University—Science B (Biomedicine & Biotechnology), 2010, 11(9), pp. 673-680.
(Continued)

*Primary Examiner* — David W Bates
(74) *Attorney, Agent, or Firm* — Lipsitz & McAllister, LLC (57) ABSTRACT

The present invention relates to a medical instrumentation for implanting an acetabular cup, comprising at least one medical guiding instrument for a first reaming tool, wherein the guiding instrument comprises a shaped body, wherein the shaped body has a patient-specific bone abutment surface facing in the distal direction and deviating from a spherical surface section, wherein the bone abutment surface is shaped so as to correspond or substantially correspond to a bone surface of the patient, and wherein a guiding shaft, defining a longitudinal axis, for guiding the first reaming tool protrudes from the shaped body and faces in the proximal direction.

20 Claims, 8 Drawing Sheets

(51) Int. Cl.
   *A61B 34/10* (2016.01)
   *A61B 90/00* (2016.01)
   *A61B 17/56* (2006.01)

(52) U.S. Cl.
   CPC ........ *A61B 90/03* (2016.02); *A61B 2017/568* (2013.01); *A61B 2034/108* (2016.02); *A61B 2090/036* (2016.02)

(56) References Cited

U.S. PATENT DOCUMENTS

| | | | |
|---|---|---|---|
| 8,603,180 B2 | 12/2013 | White et al. | |
| 8,808,302 B2* | 8/2014 | Roose | A61B 17/1746 606/96 |
| 8,932,299 B2* | 1/2015 | Bono | A61B 17/1746 606/91 |
| 8,986,309 B1* | 3/2015 | Murphy | A61B 17/1746 606/87 |
| 8,992,538 B2 | 3/2015 | Keefer | |
| 9,138,258 B2* | 9/2015 | Geebelen | A61B 17/1631 |
| 9,168,048 B2 | 10/2015 | Roose et al. | |
| 9,168,153 B2 | 10/2015 | Bettenga | |
| 9,271,744 B2* | 3/2016 | Meridew | A61B 17/1746 |
| 9,414,938 B2* | 8/2016 | Gillman | A61F 2/34 |
| 9,439,781 B2* | 9/2016 | Gibson | A61F 2/4609 |
| 9,693,878 B2* | 7/2017 | Kunz | A61B 17/1746 |
| 9,839,438 B2* | 12/2017 | Eash | A61B 17/1778 |
| 2004/0073226 A1* | 4/2004 | Cotting | A61F 2/34 606/91 |
| 2006/0079906 A1* | 4/2006 | Timperley | A61B 17/1666 606/81 |
| 2008/0009874 A1* | 1/2008 | Meridew | A61B 17/1666 606/81 |
| 2008/0300600 A1* | 12/2008 | Guelat | A61B 17/1668 606/80 |
| 2009/0163922 A1* | 6/2009 | Meridew | A61F 2/4609 606/88 |
| 2010/0082035 A1 | 4/2010 | Keefer | |
| 2010/0274253 A1* | 10/2010 | Ure | A61B 17/1746 606/91 |
| 2011/0184419 A1* | 7/2011 | Meridew | A61B 17/151 606/80 |
| 2011/0224674 A1* | 9/2011 | White | A61B 17/1617 606/91 |
| 2011/0313424 A1* | 12/2011 | Bono | A61B 17/1746 606/91 |
| 2012/0041445 A1 | 2/2012 | Roose et al. | |
| 2012/0123420 A1 | 5/2012 | Honiball | |
| 2012/0123423 A1 | 5/2012 | Fryman | |
| 2012/0143200 A1 | 6/2012 | Honiball | |
| 2012/0172884 A1 | 7/2012 | Zheng et al. | |
| 2012/0226283 A1* | 9/2012 | Meridew | A61B 17/1659 606/81 |
| 2012/0303035 A1* | 11/2012 | Geebelen | A61F 2/34 606/91 |
| 2012/0323247 A1* | 12/2012 | Bettenga | A61F 2/46 606/91 |
| 2013/0211407 A1* | 8/2013 | Geebelen | A61B 17/1631 606/80 |
| 2013/0245631 A1* | 9/2013 | Bettenga | A61B 17/1666 606/91 |
| 2014/0094816 A1 | 4/2014 | White et al. | |
| 2014/0128874 A1 | 5/2014 | Gibson et al. | |
| 2014/0135940 A1 | 5/2014 | Goldstein et al. | |
| 2014/0142578 A1 | 5/2014 | Hananouchi et al. | |
| 2014/0163564 A1* | 6/2014 | Bollinger | A61B 17/1666 606/91 |
| 2014/0358154 A1 | 12/2014 | Roose et al. | |
| 2015/0105784 A1 | 4/2015 | Bono et al. | |
| 2015/0112349 A1* | 4/2015 | Schoenefeld | A61B 17/157 606/88 |
| 2015/0190151 A1* | 7/2015 | Budhabhatti | A61B 17/1666 606/96 |
| 2015/0196307 A1 | 7/2015 | Keefer | |
| 2015/0297248 A1* | 10/2015 | Gillman | A61F 2/34 606/87 |
| 2015/0342616 A1 | 12/2015 | Fryman | |
| 2016/0038307 A1 | 2/2016 | Bettenga | |
| 2016/0250040 A1* | 9/2016 | Hermle | A61B 17/1746 606/91 |
| 2017/0273801 A1* | 9/2017 | Hodorek | A61F 2/30767 |

FOREIGN PATENT DOCUMENTS

| | | |
|---|---|---|
| EP | 2168507 | 3/2010 |
| EP | 2491873 | 8/2012 |
| JP | 2011189015 | 9/2011 |
| WO | 2010/124164 | 10/2010 |
| WO | 2010/150223 | 12/2010 |
| WO | 2011/160008 | 12/2011 |
| WO | 2012/010366 | 1/2012 |
| WO | 2012/021264 | 2/2012 |
| WO | 2012/024289 | 2/2012 |
| WO | 2012/064513 | 5/2012 |
| WO | 2012/158917 | 11/2012 |
| WO | 2012/173890 | 12/2012 |

OTHER PUBLICATIONS

Zhang, et al., "Preliminary application of computer-assisted patient-specific acetabular navigational template for total hip arthroplasty in adult single development dysplasia of the hip", The International Journal of Medical Robotics and Computer Assisted Surgery, 2011; 7: pp. 469-474.

International Search Report for corresponding application PCT/EP2014/074253, dated Jan. 22, 2015, 3 pages.

* cited by examiner

MEDICAL INSTRUMENTATION

CROSS-REFERENCE TO RELATED APPLICATIONS

This application is a continuation of international application number PCT/EP2014/074253 filed on Nov. 11, 2014 and claims the benefit of German application number 10 2013 112 497.6 filed on Nov. 13, 2013, which are incorporated herein by reference in their entirety and for all purposes.

FIELD OF THE INVENTION

The present invention relates to medical instrumentation for implanting an acetabular cup generally, and more specifically to a medical instrumentation for implanting an acetabular cup, comprising at least one medical guiding instrument for a first reaming tool.

BACKGROUND OF THE INVENTION

In particular, in patients with hip dysplasia, the existing deformities of the pelvic bone make ideal positioning of a hip joint endoprosthesis difficult. Since it is not possible to ream the existing pathological acetabulum as cup bearing, an approximately anatomical cup bearing must be reconstructed. This may, however, deviate significantly from the existing pathological situation. Although an optimal position can be planned preoperatively, the surgeon has no possibility intraoperatively of transferring the visual plan in a defined manner. Here he has to rely essentially on his experience.

SUMMARY OF THE INVENTION

In a first aspect of the invention, a medical instrumentation for implanting an acetabular cup, comprises at least one medical guiding instrument for a first reaming tool. The guiding instrument comprises a shaped body. The shaped body has a patient-specific bone abutment surface facing in the distal direction and deviating from a spherical surface section. The bone abutment surface is shaped so as to correspond or substantially correspond to a bone surface of the patient. A guiding shaft, defining a longitudinal axis, for guiding the first reaming tool protrudes from the shaped body and faces in the proximal direction.

BRIEF DESCRIPTION OF THE DRAWINGS

The foregoing summary and the following description may be better understood in conjunction with the drawing figures. There are shown in.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrumentation for implanting an acetabular cup, comprising at least one medical guiding instrument for a first reaming tool, wherein the guiding instrument comprises a shaped body, wherein the shaped body has a patient-specific bone abutment surface facing in the distal direction and deviating from a spherical surface section, wherein the bone abutment surface is shaped so as to correspond or substantially correspond to a bone surface of the patient, and wherein a guiding shaft, defining a longitudinal axis, for guiding the first reaming tool protrudes from the shaped body and faces in the proximal direction.

A medical instrumentation with a guiding instrument of such construction makes it possible, in particular, to place a first reaming tool, for example, an entrance or opening-up reamer, at the correct location and with the desired orientation, in order to form the cup bearing to be reconstructed. Since the surgeon often has a poor view of the operating site intraoperatively, the guiding instrument provides him with good support in finding the planned and desired position of the cup bearing in situ and in also maintaining it during the reaming procedure. It is thereby possible to prevent existing deformities from causing the reamer to slide off or to be pushed by bony structures into undesired positions, without the surgeon noticing this or being able to hold it in place. With the patient-specific bone abutment surface it is possible, in particular, to clearly position the shaped body on the pelvic bone of the patient and to then guide the first reaming tool with the guiding shaft into the desired position, in order to form the planned cup bearing. The optimal cup bearing can, for example, be planned preoperatively on the basis of one or more X-rays. On the basis of this, the patient-specific bone abutment surface, for example, can be formed. The proposed guiding instrument is, in particular, well-suited for use with obese patients as palpation of landmarks is difficult in these and, therefore, error-prone. The guiding instrument also makes it possible to mechanically guide the first reaming tool. Known systems which only provide the surgeon with optical guidance on a screen, in particular, also with the support of a navigation system, are, however, unable to prevent the reaming tool from sliding off the pelvic bone. The guiding instrument also makes it possible, in particular, when it has a shaped body without any through-openings, to prevent additional injury to the bottom of the acetabulum. If, for example, the shaped body is fixed with a pin or K-wire, it can be driven deeper into the pelvis during the reaming owing to increased friction or getting caught and thereby cause serious injuries. This is effectively prevented with the proposed guiding instrument. In addition, the guiding shaft can be made of such stable construction, i.e., have a sufficiently large diameter, to form a sufficiently stable mechanical guide, which can, therefore, prevent snapping-off or bending during the reaming.

It is expedient for the patient-specific bone abutment surface to be arranged or constructed so as to face in the distal direction, and for the guiding shaft to be arranged or constructed so as to face in the proximal direction. The guiding instrument may as a whole be of one-piece construction. A multipart construction is also conceivable. For example, it would be conceivable to offer the shaped body with the shaft as one part and to provide a separate element comprising the bone abutment surface, which can be positioned on the shaped body. In this way, the manufacture of the patient-specific guiding instrument can be simplified. A guiding instrument formed from one piece is particularly stable.

It is advantageous for the shaped body to have a stop acting in the distal direction for a reaming tool. In this way, it can be precisely specified how far the reaming tool can be moved in the direction towards the acetabulum of the patient. The depth of the cup bearing to be reamed can, therefore, also be specified.

A stop can be formed in a particularly simple way when it has a stop surface facing in the proximal direction. The first reaming tool, for example, can then enter into abutment with this stop surface and prevent further penetration into the pelvis.

The stop surface is expediently flat or substantially flat. This is particularly easy to manufacture and also has the advantage that friction can be minimized between the stop surface and the reaming tool.

To further improve the guiding of the reaming tool, it is advantageous for the stop surface to define a plane which extends transversely to the longitudinal axis. In particular, the plane can extend perpendicularly to the longitudinal axis. The desired orientation for the cup bearing to be formed can, therefore, be precisely specified. In particular, it is expedient for the guiding shaft to be of such length that, in particular, in the case of minimally invasive access, it protrudes from the patient's body when the patient-specific bone abutment surface lies against the patient's acetabulum.

In accordance with a further preferred embodiment of the invention, it may be provided that the stop surface adjoins the patient-specific bone abutment surface, and that a transition between the stop surface and the patient-specific bone abutment surface is tangentially discontinuous. Such a configuration is particularly easy to manufacture. For example, a proximal end of the shaped body can be milled off or abraded for formation of the stop surface.

It is advantageous for a width of the stop surface to vary as a function of a circumferential angle. This allows a surgeon to immediately recognize that the bone abutment surface has a distinct shape and so the shaped body can only be positioned in a specific manner with positive fitting on the acetabulum.

To obtain particularly good guidance for the reaming tool, it is advantageous for the bone abutment surface to be at least partially adapted to a contour of the acetabulum of the patient. It is preferably fully adapted to the contour of the acetabulum, more specifically, in a surface area which the shaped body covers.

The bone abutment surface preferably has a contour which corresponds at least to a portion of the fossa and/or to a portion of the acetabular notch. For example, the shaped body can thus be constructed in the form of a negative print of the fossa and/or of a portion of the acetabular notch.

The instrumentation can be manufactured particularly easily and cost-effectively if the shaped body is of dish-shaped construction and has a constant or substantially constant width.

The bone abutment surface and/or the shaped body are preferably manufactured by molding or 3-D printing. For molding the shaped body, in particular, a mold on the basis of patient-specific contour data of the pathological acetabulum can be manufactured, for example, from a metal or a plastic material. During the 3-D printing of the bone abutment surface and/or of the shaped body, patient-specific, noninvasively determined contour data can be directly used to form the bone abutment surface and/or the shaped body.

In accordance with a further preferred embodiment of the invention, it may be provided that the bone abutment surface of the shaped body defines bone abutment surface contour data which correspond or substantially correspond to non-invasively determined bone contour data of the patient. In particular, the bone contour data of the patient can originate from X-ray or magnetic resonance images of the patient. In other words, the bone abutment surface of the shaped body is, in particular, formed exactly so as to form a negative shape of the pathological acetabulum in that area where the planned cup bearing is to be formed for the hip joint endoprosthesis.

It is expedient for the guiding shaft to be connected to the shaped body in a non-releasably or releasably connectable manner. The non-releasable variant has the advantage that the alignment of the guiding shaft relative to the bone abutment surface cannot be inadvertently altered. A releasable connectability does, however, allow the guiding shaft to be chosen shorter or longer depending on the patient.

It is advantageous for the instrumentation to comprise a coupling device for temporarily coupling the shaped body to the guiding shaft. The guiding shaft and the shaped body can be easily connected to or released from each other with the coupling device.

The manufacture of the instrumentation is simplified, in particular, by the coupling device comprising at least one first coupling element and at least one second coupling element, by the at least one first and second coupling elements being constructed so that they correspond to each other and are in engagement in a coupling position and in disengagement in a release position. The first and second coupling elements can thus be easily and securely connected to each other in a defined manner.

The first and second coupling elements can be easily and securely coupled if the at least one first coupling element is constructed in the form of a coupling receptacle and the at least one second coupling element in the form of a coupling projection.

Furthermore, it may be expedient for the at least one first coupling element to have an internal thread section and the at least one second coupling element to have a corresponding external thread section. The two coupling elements can thus be easily coupled to each other by screwing. In other words, the guiding shaft can, for example, be screwed onto the shaped body.

It is advantageous for the least one first coupling element to be arranged or constructed on the shaped body, and for the at least one second coupling element to be arranged or constructed on the guiding shaft. This allows the shaped body and the guiding shaft to be connected to each other and released from each other again as required.

The guiding shaft is expediently constructed in the form of an elongate cylindrical rod. Such a guiding shaft enables simple and secure guidance of an, in particular, rotating reaming tool.

The instrumentation preferably comprises a first reaming tool and/or a second reaming tool. The two reaming tools may, in particular, be of different construction, for example, for preparation of the acetabulum for insertion of different cups of the hip joint endoprostheses.

It is expedient for the first reaming tool to be constructed in the form of an entrance reamer with a cannulated reamer shaft which defines a reamer shaft longitudinal axis and is constructed to receive the guiding shaft of the medical guiding instrument. With the first reaming tool of such construction, it is possible to push it over the guiding shaft and thus form a first entrance drill hole or opening-up drill hole on the acetabulum. Movement of the first reaming tool in the distal direction is preferably delimited by the shaped body of the guiding shaft. For optimal guidance, an inner diameter of a longitudinal through-opening of the cannulated reamer shaft corresponds substantially to an outer diameter of the guiding shaft.

It is advantageous for the entrance reamer to have a reamer head, for the reamer head to have a machining surface closed within itself, and for the machining surface to form a section of a spherical surface. With such a reamer head, an entrance drill hole can be formed on the pathological acetabulum with a contour which corresponds to a ring surface of a spherical surface. This can be used, in particular, to guide a conventional acetabulum reamer having a spherical head.

Particularly good and safe machining of the acetabulum is possible if the machining surface carries or comprises a plurality of cutting elements. In particular, the cutting elements can be formed from the same material as the reamer head or from a different material which has advantageous characteristics for machining bones.

It is expedient for the reamer head to have a reamer head stop surface facing in the distal direction. This can interact, in particular, with the stop surface on the shaped body facing in the proximal direction in order to delimit penetration of the reamer head into the pelvic bone.

The instrumentation can be manufactured particularly easily if the reamer head stop surface is of flat or substantially flat construction and extends transversely to the reamer shaft longitudinal axis. In particular, it can thus lie with surface-to-surface contact against a stop surface of the shaped body, which defines a plane extending perpendicularly to the longitudinal axis of the guiding shaft.

In accordance with a further preferred embodiment of the invention, it may be provided that the reamer head has an end face facing in the proximal direction, which is of flat or substantially flat construction. In particular, the end face can extend transversely to the reamer shaft longitudinal axis and define an end face plane containing a sphere center of the spherical surface. In this way, the largest diameter of the reamer head is defined in the area of the end face facing in the proximal direction.

It is advantageous for the second reaming tool to be constructed in the form of an acetabulum reamer with a spherical acetabulum reamer head and an acetabulum reamer shaft protruding in the proximal direction. If an entrance drill hole was formed on the acetabulum with the entrance reamer in a first step, the cup bearing can be finished in the desired manner with the acetabulum reamer in a second step.

Figure 1:
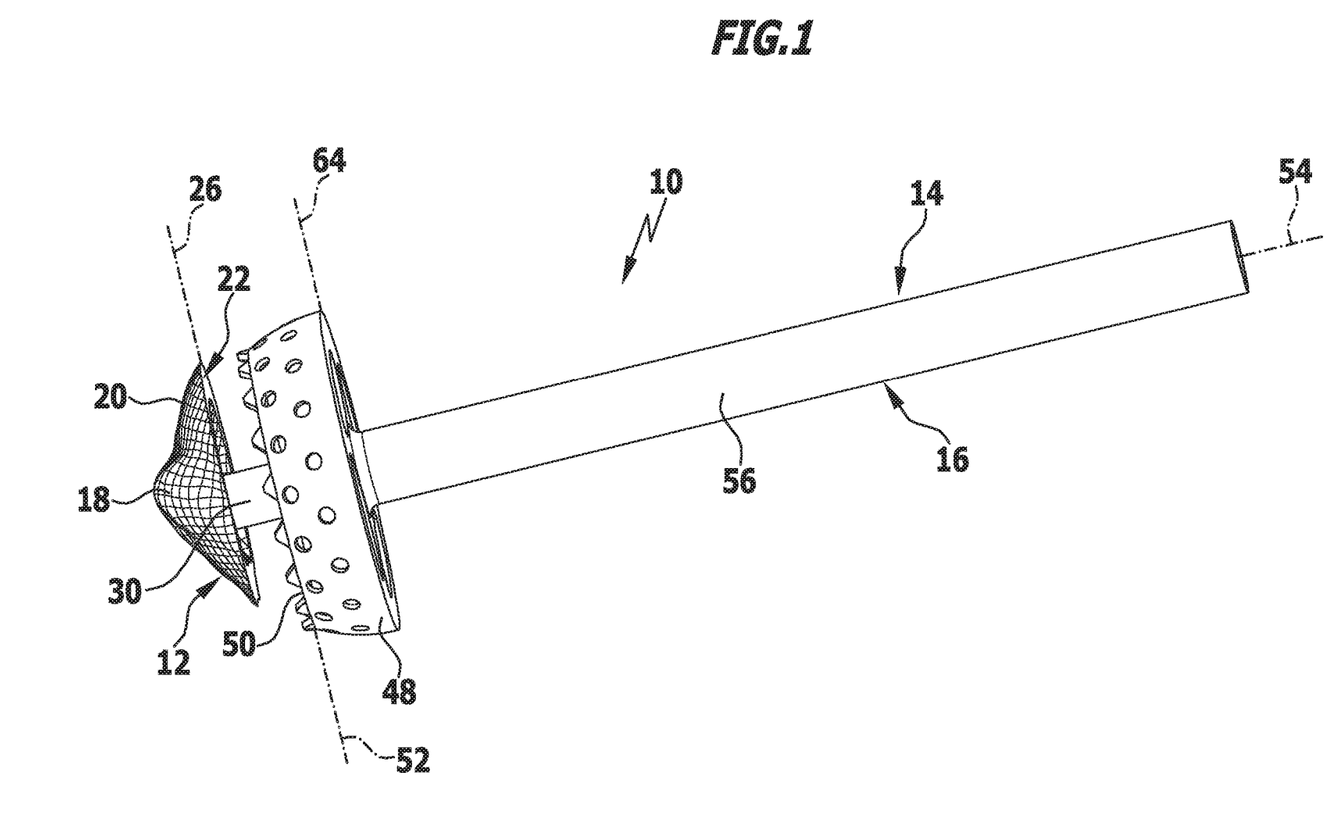
FIG. 1 a schematic side view of a medical instrumentation comprising a guiding instrument and an entrance reamer.

A medical instrumentation, denoted in its entirety by reference numeral 10, is shown schematically in FIG. 1. It comprises a medical guiding instrument 12 and a first reaming tool 14 in the form of an entrance or opening-up reamer 16.

The guiding instrument 12 comprises a shaped body 18 having a patient-specific bone abutment surface 20 facing in the distal direction.

The shaped body 18 is preferably of dish-shaped configuration without any through-holes and has a stop 22 acting in the distal direction for the first reaming tool 14. The stop 22 has a stop surface 24 facing in the proximal direction. The stop surface 24 is of flat construction and defines a plane 26 extending transversely to a longitudinal axis 28 of the guiding instrument 12. The longitudinal axis 28 is defined by a guiding shaft 30 which protrudes from the shaped body 18 and faces in the proximal direction. The shaped body 18 preferably has a constant or substantially constant thickness.

Figure 2:
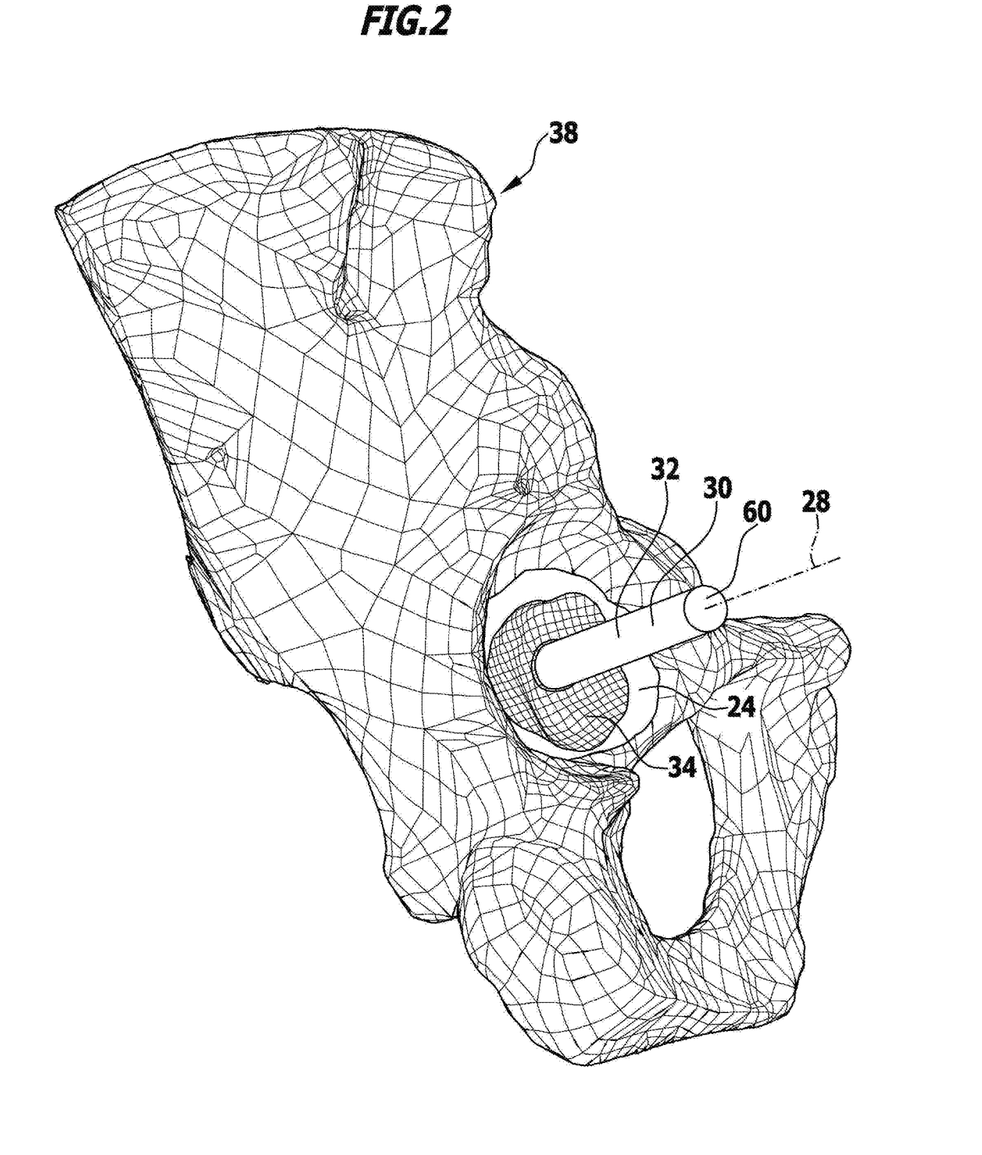
FIG. 2 a schematic view of the guiding instrument positioned on the pathological acetabulum.
Figure 3:
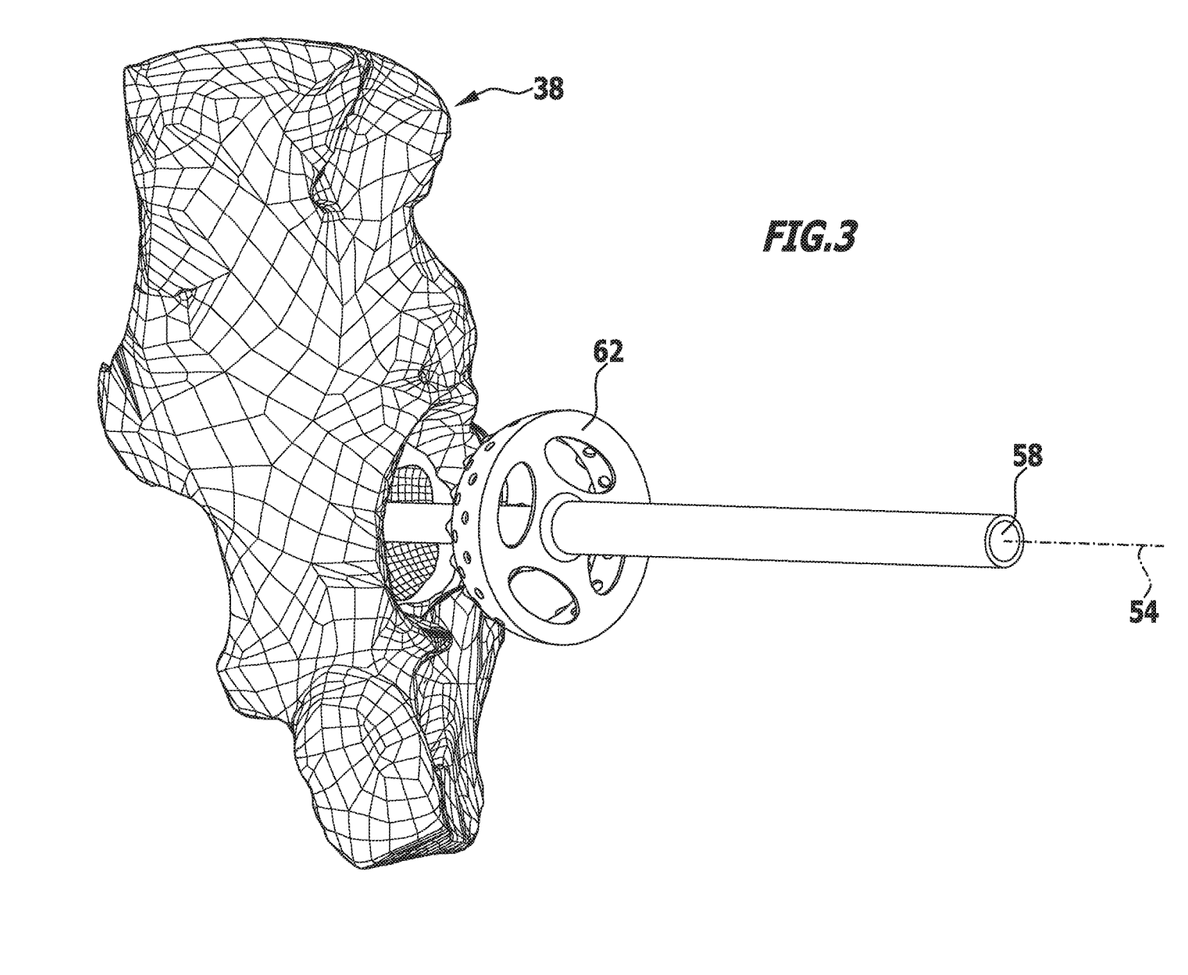
FIG. 3 a schematic perspective view while placing the entrance reamer on the guiding shaft of the guiding instrument positioned on the acetabulum.
Figure 4:
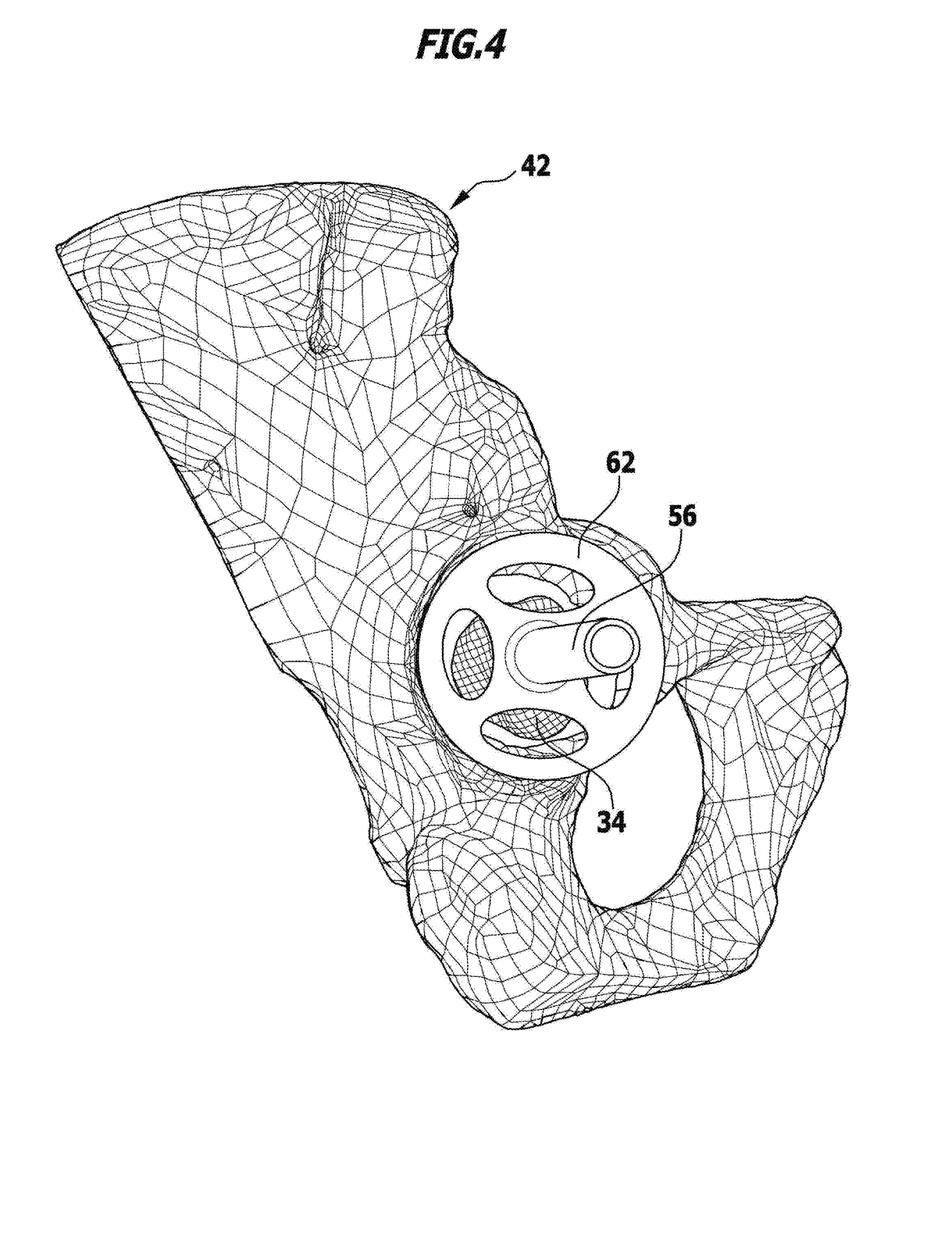
FIG. 4 a schematic perspective view of the entrance reamer placed on the guiding instrument while reaming an entrance drill hole on the acetabulum.
Figure 5:
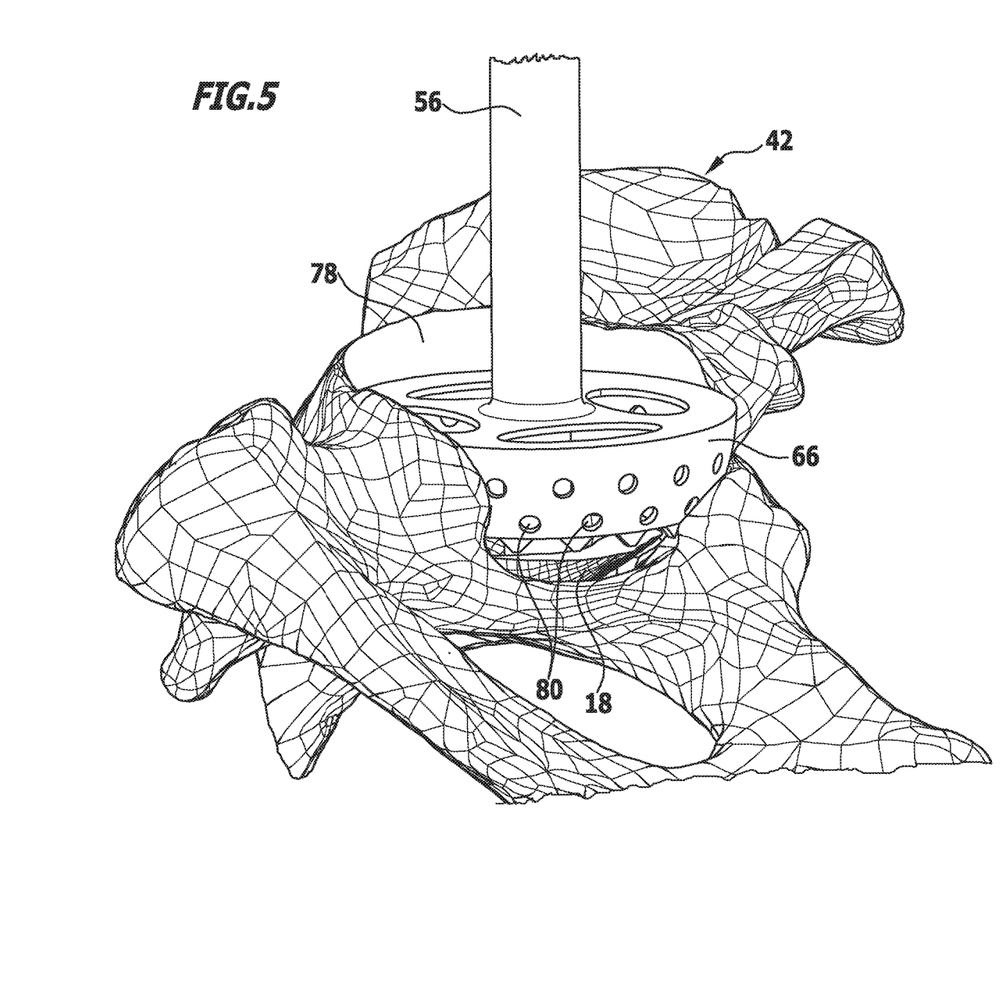
FIG. 5 a schematic perspective view of the arrangement from FIG. 4 from the side.
Figure 6:
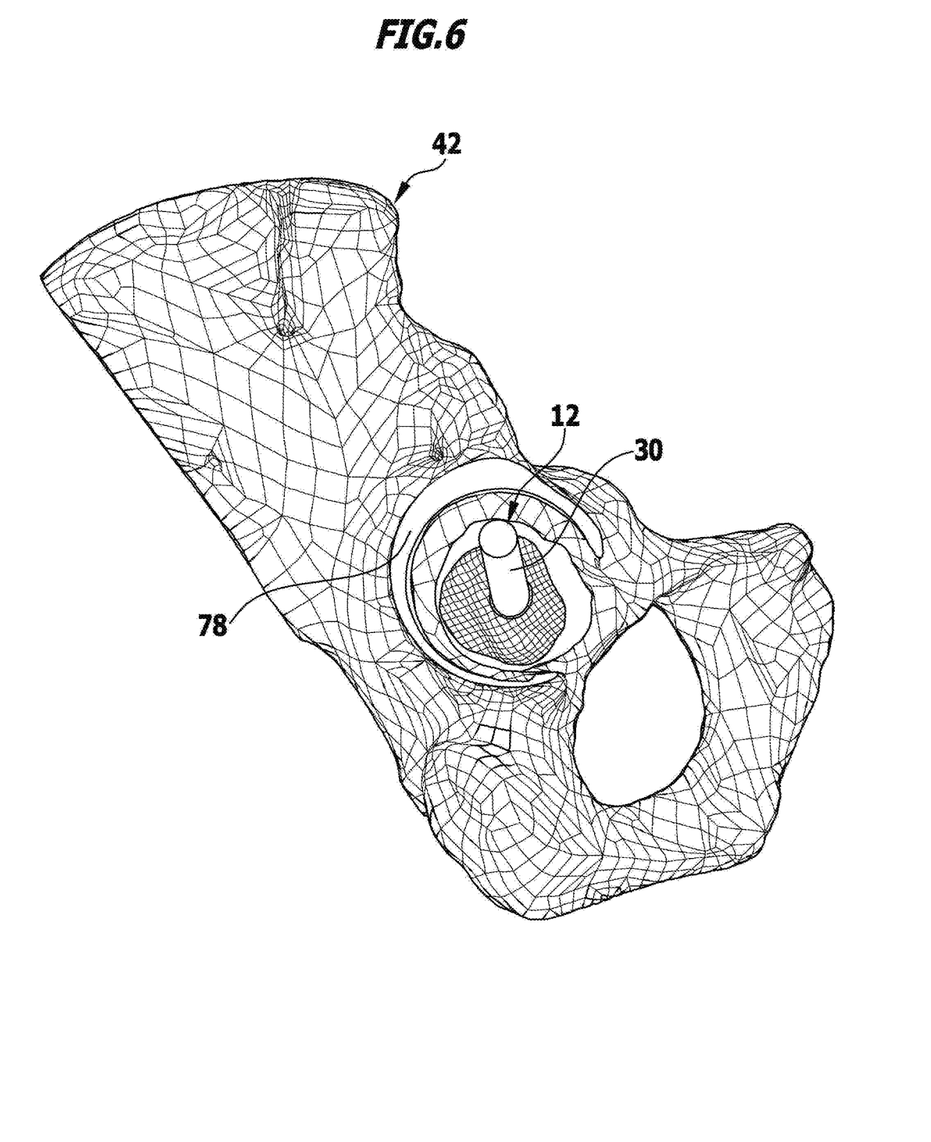
FIG. 6 a schematic perspective view of the guiding instrument positioned on the pelvic bone with prepared entrance drill hole after removal of the entrance reamer.

As can be clearly seen, for example, in FIG. 2, a width of the stop surface 24 varies as a function of a circumferential angle. In other words, the stop surface 24 is not constructed in the form of a circular ring concentric with the longitudinal axis 28, but in the form of a ring surface which is delimited both on the inside and on the outside by an irregular delimitation line. Furthermore, a transition from the bone abutment surface 20 to the stop surface 24 adjoining it is tangentially discontinuous.

The guiding shaft 30 is constructed in the form of an elongate, cylindrical rod 32. It extends away from a side surface 34, facing in the proximal direction, of the shaped body 18.

The bone abutment surface 20 is formed so as to correspond to a bone surface 36 of the pelvic bone 38 of the patient in that area in which the cup bearing 40 for the cup of the hip joint endoprosthesis to be implanted is to be placed. The bone abutment surface 20 is, therefore, adapted to a contour of the acetabulum 42 of the patient. In particular, it has a contour which corresponds to the fossa 44, to at least a portion thereof and/or to the acetabular notch 46 or to a portion thereof.

The bone abutment surface 20 on the shaped body 18 and/or the shaped body 18 are preferably manufactured by molding or 3-D printing. For the molding, a mold is formed on the basis of noninvasively determined bone contour data of the patient. For example, the bone contour data may originate from X-ray and/or magnetic resonance images of the acetabulum 42 of the patient. Directly digitalized X-ray images can, for example, be further processed to form printing data for a 3-D printer, with which the bone abutment surface 20 can then be printed on a carrier or as part of the shaped body 18 together with the latter, optionally also together with the guiding shaft 30. In this way, a bone abutment surface 20 can then be constructed, which defines the bone abutment surface contour data corresponding to the noninvasively determined bone contour data of the patient.

The guiding instrument 12 serves to guide the entrance reamer 16. The entrance reamer 16 has a reamer head 48 with a reamer head stop surface 50 facing in the distal direction. The reamer head stop surface 50 is preferably flat and defines a stop plane 52 which extends transversely, in particular, perpendicularly, to a reamer shaft longitudinal axis 54, which is defined by a reamer shaft 56 of the entrance reamer 16. The reamer shaft 56 is of cannulated construction and has a through-hole 58 extending concentrically with the reamer shaft longitudinal axis 54. The inner diameter of the through-hole 58 is adapted to an outer diameter of the guiding shaft 30 and preferably corresponds substantially thereto. This configuration enables the entrance reamer 16 to be pushed from the proximal direction over a proximal end 60 of the guiding shaft 30 onto the guiding shaft 30.

Furthermore, the reamer head 48 has an end face 62 facing in the proximal direction. The end face 62 is preferably of flat construction and defines an end face plane 64, which runs transversely, in particular, perpendicularly, to the reamer shaft longitudinal axis 54. The reamer head 48 also has a machining surface 66 which is closed within itself in the shape of a ring. The machining surface 66 forms a section of a spherical surface. The machining surface 66 carries a plurality of cutting elements 80 which are constructed, for example, in the form of reaming teeth protruding in the radial direction from the machining surface 66. Optionally, the end face 62 is of such configuration that a sphere center of the spherical surface defined by the machining surface 66 lies on the end face plane 64.

Figure 7:
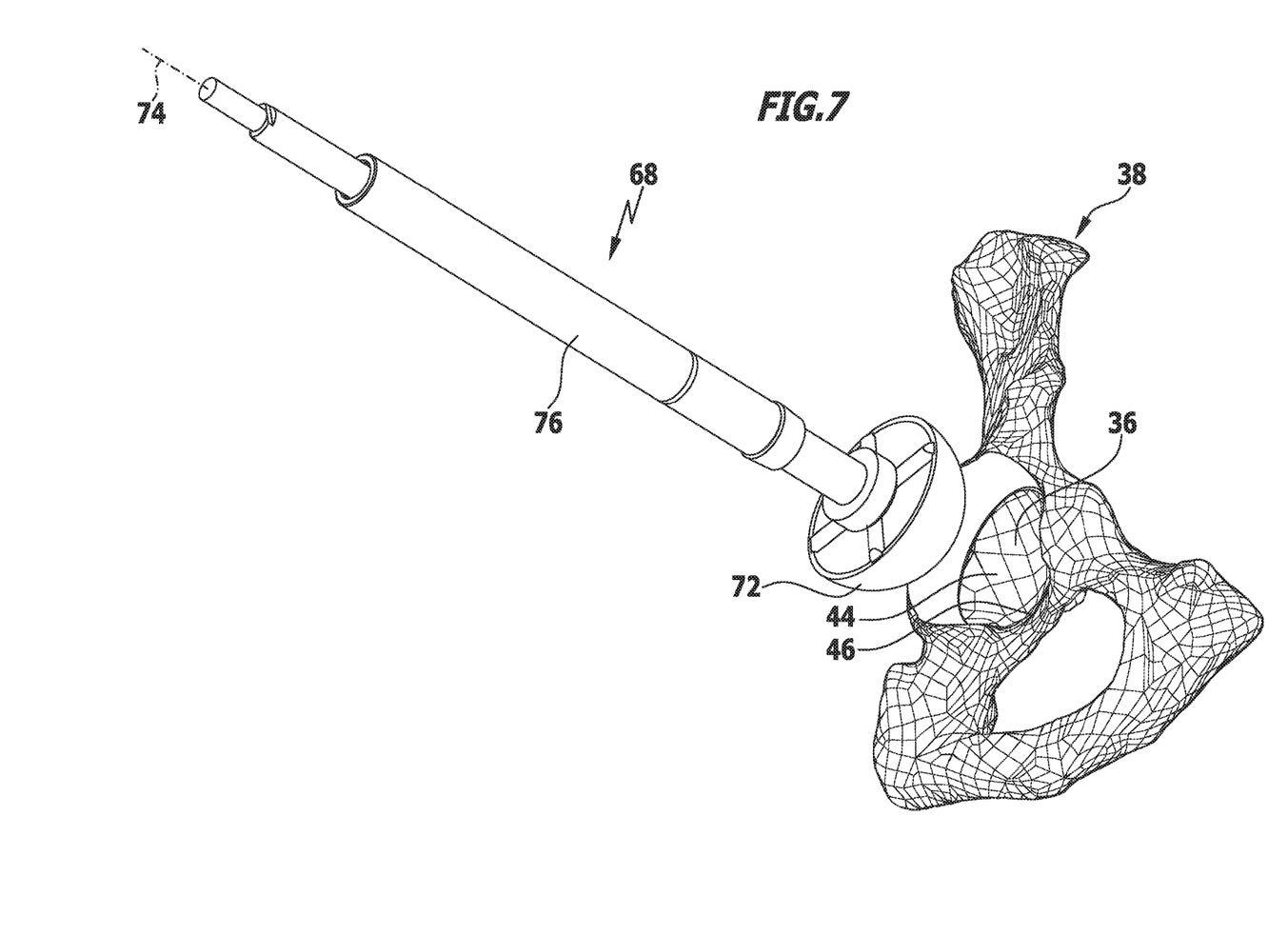
FIG. 7 a schematic perspective view while advancing an acetabulum reamer to the prepared entrance drill hole after removal of the guiding instrument.
Figure 8:
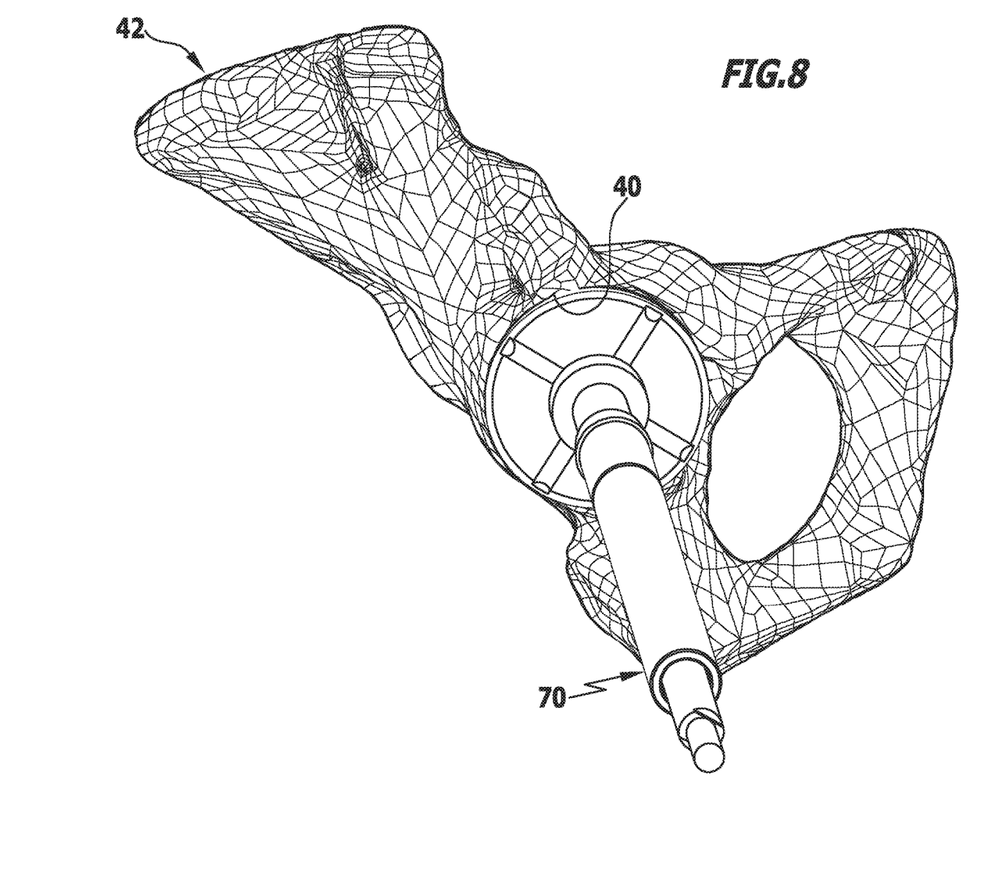
FIG. 8 a schematic perspective view of the pelvis while preparing the cup bearing with the acetabulum reamer.

The instrumentation 10 further comprises a second reaming tool 68 which is constructed in the form of an acetabulum reamer 70. The acetabulum reamer 70 comprises a substantially spherical acetabulum reamer head 72 and an elongate acetabulum reamer shaft 76 protruding in the proximal direction from the acetabulum reamer head 72 and defining an acetabulum reamer longitudinal axis 74. The acetabulum reamer 70 may, in particular, be constructed in the form of a conventional acetabulum reamer.

The way in which the instrumentation 10 works and the way in which to proceed when preparing the planned cup bearing 40 will be explained in greater detail hereinbelow in conjunction with FIGS. 2 to 8.

The guiding instrument 12 manufactured on the basis of the patient-specific bone contour data is introduced with the shaped body 18 first into the patient's body and positioned with the entire surface on the corresponding bone surface 36. This step is shown schematically in FIG. 2.

Next, the entrance reamer 16 is pushed with its cannulated reamer shaft 56 onto the guiding shaft 30 of the guiding instrument 12, and the reamer head 48 is advanced to the pelvic bone 38. This is shown by way of example in FIGS. 3 and 4.

The entrance reamer 16 can now be set in rotation by a suitable drive in order to prepare an entrance drill hole 78 on the acetabulum 42. The entrance drill hole 78 has a shape which corresponds to a hollow-spherical surface area, which is substantially defined by the machining surface 66. This step is shown schematically, in particular, in FIG. 5.

After the entrance drill hole 78 has been made, the entrance reamer 16 can be removed again. This procedural step is shown schematically in FIG. 6.

The guiding instrument 12 can now also be removed and the actual cup bearing 40 prepared with the acetabulum reamer 70. This then has a substantially hollow-spherical shape and serves to receive the cup of the hip joint endoprosthesis.

The guiding instrument 12 may be completely or partly manufactured from a sterilizable plastic material or a metal.

Optionally, it is also possible to construct the guiding shaft 30 and the shaped body 18 separately from each other and to provide a corresponding coupling device for connecting these two parts to each other. This optional design makes it possible, for example, to manufacture the guiding shaft 30 from a metal and to reuse it, so that only the shaped body 18 with a corresponding coupling element for connection to the guiding shaft 30 has to be molded or printed. The coupling elements may be constructed, in particular, in the form of projections or corresponding receptacles, which may be provided, for example, with inner and outer thread sections corresponding to one another.

LIST OF REFERENCE NUMERALS

10: instrumentation
12: guiding instrument
14: first reaming tool
16: entrance reamer
18: shaped body
20: bone abutment surface
22: stop
24: stop surface
26: plane
28: longitudinal axis
30: guiding shaft
32: rod
34: side surface
36: bone surface
38: pelvic bone
40: cup bearing
42: acetabulum
44: fossa
46: acetabular notch
48: reamer head
50: reamer head stop surface
52: stop plane
54: reamer shaft longitudinal axis
56: reamer shaft
58: through-hole
60: end
62: end face
64: end face plane
66: machining surface
68: second reaming tool
70: acetabulum reamer
72: acetabulum reamer head
74: acetabulum reamer longitudinal axis
76: acetabulum reamer shaft
78: entrance drill hole
080: cutting element

What is claimed is:

1. Medical instrumentation for implanting an acetabular cup, comprising:
    a first reaming tool, the first reaming tool comprising an entrance reamer with a cannulated reamer shaft which defines a reamer shaft longitudinal axis,
    at least one medical guiding instrument for the first reaming tool, the guiding instrument comprising a shaped body, the shaped body comprising a patient-specific bone abutment surface facing in a distal direction, the bone abutment surface deviating from a spherical surface section and being shaped so as to correspond or substantially correspond to a bone surface of the patient, and
    a guiding shaft, which defines a guiding shaft longitudinal axis, for guiding the first reaming tool, the guiding shaft protruding from the shaped body and facing in a proximal direction, and
    wherein the first reaming tool is constructed to receive the guiding shaft of the medical guiding instrument.

2. The medical instrumentation in accordance with claim 1, wherein at least one of:
    the patient-specific bone abutment surface is arranged or constructed so as to face in the distal direction, and the guiding shaft is arranged or constructed so as to face in the proximal direction, and
    the shaped body has a stop acting in the distal direction for the reaming tool.

3. The medical instrumentation in accordance with claim 1, wherein:
    the shaped body has at least one stop acting in the distal direction for the reaming tool, and
    the at least one stop has a stop surface facing in the proximal direction.

4. The medical instrumentation in accordance with claim 3, wherein the stop surface at least one of:
is of flat or substantially flat construction,
and
defines a plane which extends transversely to the reamer shaft longitudinal axis.

5. The medical instrumentation in accordance with claim 4, wherein at least one of:
the stop surface adjoins the patient-specific bone abutment surface, and a transition between the stop surface and the patient-specific bone abutment surface is tangentially discontinuous,
and
a width of the stop surface varies as a function of a circumferential angle.

6. The medical instrumentation in accordance with claim 1, wherein the bone abutment surface is at least partially adapted to a contour of an acetabulum of the patient.

7. The medical instrumentation in accordance with claim 1, wherein the bone abutment surface has a contour which corresponds at least to a portion of a fossa and/or to a portion of an acetabular notch of the patient.

8. The medical instrumentation in accordance with claim 1, wherein the shaped body is of dish-shaped construction and has a constant or substantially constant thickness.

9. The medical instrumentation in accordance with claim 1, wherein the bone abutment surface and/or the shaped body are manufactured by molding or 3-D printing.

10. The medical instrumentation in accordance with claim 1, wherein the bone abutment surface of the shaped body defines bone abutment surface contour data which correspond or substantially correspond to one of:
(a) noninvasively determined bone contour data of the patient,
or
b) noninvasively determined bone contour data of the patient from X-ray or magnetic resonance images.

11. The medical instrumentation in accordance with claim 1, wherein at least one of:
the guiding shaft is connected to the shaped body in a non-releasably or releasably connectable manner,
and
the medical instrumentation further comprises a coupling device for temporarily coupling the shaped body to the guiding shaft.

12. The medical instrumentation in accordance with claim 1, further comprising a coupling device for temporarily coupling the shaped body to the guiding shaft, wherein:
the coupling device comprises at least one first coupling element and at least one second coupling element, and
the at least one first and second coupling elements are constructed so that they correspond to each other and are in engagement in a coupling position and in disengagement in a release position.

13. The medical instrumentation in accordance with claim 12, wherein the at least one first coupling element at least one of:
is constructed in the form of a coupling receptacle and the at least one second coupling element in the form of a coupling projection,
and
has an internal thread section and the at least one second coupling element has a corresponding external thread section,
and
is arranged or constructed on the shaped body, and the at least one second coupling element is arranged or constructed on the guiding shaft.

14. The medical instrumentation in accordance with claim 1, wherein
the guiding shaft is constructed in the form of an elongate cylindrical rod.

15. The medical instrumentation in accordance with claim 1, wherein:
the entrance reamer has a reamer head,
the reamer head has a machining surface closed within itself, and
the machining surface forms a section of a spherical surface.

16. The medical instrumentation in accordance with claim 15, wherein at least one of:
the machining surface carries or comprises a plurality of cutting elements, and
the reamer head has a reamer head stop surface facing in the distal direction.

17. The medical instrumentation in accordance with claim 16, wherein the reamer head stop surface is of flat or substantially flat construction and extends transversely to the reamer shaft longitudinal axis.

18. The medical instrumentation in accordance with claim 15, wherein the reamer head has an end face facing in the proximal direction, which is one of:
(a) of flat or substantially flat construction,
(b) of flat or substantially flat construction and extends transversely to the reamer shaft longitudinal axis, or
(c) of flat or substantially flat construction, extends transversely to the reamer shaft longitudinal axis, and defines an end face plane containing a sphere center of the spherical surface.

19. The medical instrumentation in accordance with claim 1, further comprising a second reaming tool.

20. The medical instrumentation in accordance with claim 19, wherein the second reaming tool is constructed in the form of an acetabulum reamer comprising a spherical acetabulum reamer head and an acetabulum reamer shaft protruding in the proximal direction.

* * * * *